United States Patent [19]

Arndt et al.

[11] Patent Number: 4,540,832
[45] Date of Patent: Sep. 10, 1985

[54] PROCESS FOR THE PREPARATION OF 6-CHLORO-2,4-DINITROPHENOL

[75] Inventors: Otto Arndt, Hofheim am Taunus; Theodor Papenfuhs, Frankfurt am Main, both of Fed. Rep. of Germany

[73] Assignee: Hoechst Aktiengesellschaft, Fed. Rep. of Germany

[21] Appl. No.: 604,072

[22] Filed: Apr. 26, 1984

[30] Foreign Application Priority Data

Apr. 30, 1983 [DE] Fed. Rep. of Germany ....... 3315798

[51] Int. Cl.³ .................. C07C 79/28; C07C 79/32
[52] U.S. Cl. .................................. 568/711; 568/709; 568/710
[58] Field of Search ............... 568/709, 711, 713, 710, 568/704

[56] References Cited

U.S. PATENT DOCUMENTS 1,398,998  12/1921  Bradshaw ........................... 568/711
4,473,713   9/1984  Ratton ................................ 568/711

Primary Examiner—Werren B. Lone

Attorney, Agent, or Firm—Connolly and Hutz

[57] ABSTRACT

A process for the preparation of 6-chloro-2,4-dinitrophenol in a high yield and in a high degree of purity by saponifying 2,4-dinitrochlorobenzene and/or 2,4-dinitrophenyl alkyl ethers of the formula

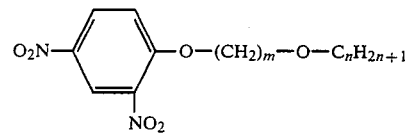

in which m denotes the number 2, 3 or 4 and n denotes the number 1 or 2, by means of aqueous sodium hydroxide or potassium hydroxide solution and chlorinating the resulting 2,4-dinitrophenol with sodium hypochlorite, which comprises chlorinating the 2,4-dinitrophenol, without prior isolation as an intermediate, in aqueous suspension at a pH value of 3.5–7 by means of chlorine bleach liquor at temperatures of 5° to 20° C.

8 Claims, No Drawings

PROCESS FOR THE PREPARATION OF 6-CHLORO-2,4-DINITROPHENOL

The invention relates to the preparation of 6-chloro-2,4-dinitrophenol from 2,4-dinitrochlorobenzene and/or 2,4-dinitrophenyl alkyl ethers of the formula

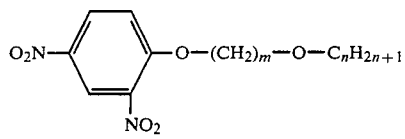

in which m denotes the number 2, 3 or 4 and n denotes the number 1 or 2, via the stage of 2,4-dinitrophenol or the sodium salt thereof (by saponification) and chlorination of the last-mentioned compound.

The two stages, saponification and chlorination, are known as individual steps. Thus the saponification is described in "Grundlegende Operationen der Farbenchemie" ["Fundamental Operations in Dyestuffs Chemistry"] by Fierz-David-Blangley, 8th Edition (1952), page 329, and in BIOS Final Report No. 986, Item 22, page 183, and the chlorination is described in Beilstein 6, E II 247 and also in Beilstein 6, 259.

The first-mentioned Beilstein literature reference states that 6-chloro-2,4-dinitrophenol is formed, together with other products, when sodium hypochlorite acts on 2,4-dinitrophenol in dilute hydrochloric acid at 15°–20° C. The last-mentioned Beilstein literature reference states that a little 4-chloro-2,6-dinitrophenol and a great deal of 6-chloro-2,4-dinitrophenol are formed if chlorine is passed into a boiling mixture of picnic acid, water and iodine until chloropicrin manifests itself.

As can be seen, the chlorination processes forming part of the state of the art, either using elementary chlorine or using sodium hypochlorite, are carried out in a fairly strongly acid medium, and appreciable amounts of by-products are formed. Our own attempts to carry out chlorination by means of elementary chlorine in concentrated hydrochloric acid have not been successful, because 2,4-dichloro-6-nitrophenol, 2,6-dichloro-4-nitrophenol and a number of unknown compounds are formed in this reaction by the replacement of nitro groups by chlorine atoms. Chlorination by means of sodium hypochlorite in an aqueous alkaline solution did not attain the objective either, because in this case no chlorination takes place.

Another possible means of preparing 6-chloro-2,4-dinitrophenol is described in FIAT 1313 I 100; in this process o-chlorophenol is sulfonated and the resulting 2-chlorophenol-4-sulfonic acid is nitrated using nitric acid, with elimination of the sulfonic acid group, to give 6-chloro-2,4-dinitrophenol. This method of preparation is not economical because of the necessity, associated therewith, to work up the waste acids produced.

It has now been found that 6-chloro-2,4-dinitrophenol can be prepared in a high yield and in a high degree of purity by saponifying 2,4-dinitrochlorobenzene and/or 2,4-dinitrophenyl alkyl ethers of the formula

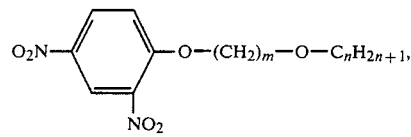

in which m denotes the number 2, 3 or 4 and n denotes the number 1 or 2, by means of aqueous sodium hydroxide or potassium hydroxide solution and chlorinating the resulting 2,4-dinitrophenol with sodium hypochlorite, by chlorinating 2,4-dinitrophenol, without previous isolation as an intermediate, in aqueous suspension at a pH value of 3.5–7, preferably 4–4.5, with chlorine bleach liquor at temperatures of 5° to 20° C., preferably 8°–12° C.

Chlorine bleach liquor is to be understood here to mean an aqueous solution of sodium hypochlorite and sodium chloride which can be prepared by passing chlorine into cold, aqueous sodium hydroxide solution. The technical chlorine bleach liquor has a strength of 13% by weight, which means that this chlorine bleach liquor contains 150 g of active chlorine per liter. As well as this technical chlorine bleach liquor, which is preferably employed in the process of the present invention, it is also possible to use chlorine bleach liquors of lower concentrations in accordance with the process. (Gmelins Handbuch der anorganischen Chemie ["Gmelin's Handbook of Inorganic Chemistry"] 6 (1927), page 293; Ullmanns Encyklopädie der technischen Chemie ["Ullman's Encyclopaedia of Industrial Chemistry"] 9, 4th Edition (1975), page 544).

Since the chlorination of 2,4-dinitrophenol by means of sodium hypochlorite in dilute hydrochloric acid in accordance with the literature reference quoted earlier in the text does not lead to a pure product, and the yield also leaves something to be desired, and our own attempts to carry out chlorination by means of sodium hypochlorite have not attained the objective either in concentrated hydrochloric acid or in an alkaline medium, it must be considered surprising that the chlorination according to the invention by means of sodium hypochlorite in the pH range mentioned (slightly acid through neutral to very slightly alkaline) is successful.

Details and preferred embodiments of the process according to the invention are additionally described below:

As far as the saponification of 2,4-dinitrochlorobenzene or 2,4-dinitrophenyl alkyl ether is concerned, it is advisable to carry out the saponification with the dilute aqueous sodium hydroxide or potassium hydroxide solution within the pH range of 11–13 in air or in the presence of small quantities of an oxidizing agent, such as oxygen, hydrogen peroxide or sodium hypochlorite [c.f. in this respect HOUBEN-WEYL, VI/1c 1976, page 181; German Auslegeschrift No. 1,543,952 (1970), U.S. Pat. No. 3,283,011 (1962), and J.Am.Chem.Soc. 95 (1973) 7, pages 2133–2136; Japanese Pat. No. 55/79,350 (1978); and Japanese Preliminary Published Application No. 80-79350 (1980)].

In view of the additional oxidizing action of sodium hypochlorite, it is preferable to use this compound in an equivalent amount or in an excess of only up to about 20 mole %, in each case relative to the dinitrophenol to be chlorinated. The use of a greater excess of sodium hypochlorite results in reduced yields.

Before the metered addition of the sodium hypochlorite solution to the aqueous suspension of the 2,4-dinitrophenol obtained, it is necessary to neutralize with a mineral acid, for example hydrochloric acid, the excess of sodium hydroxide or potassium hydroxide solution which has been used in the saponification of the 2,4-dinitrochlorobenzene or 2,4-dinitrophenyl alkyl ether to give the corresponding sodium phenates or potassium phenates, respectively.

Auxiliaries for promoting the fine distribution of the reactants, such as surfactants, or auxiliaries for accelerating the chlorination reaction, such as iron(III) chloride and iodine in combination, can be added to the reaction mixture.

Since one equivalent of sodium hydroxide (NaOH) is formed in the chlorination of 2,4-dinitrophenol with sodium hypochlorite (NaOCl), it is advisable to add to the reaction mixture, as early as before the metered addition of the aqueous sodium hypochlorite solution, the amount of mineral acid, for example hydrochloric acid, required to neutralize this equivalent of NaOH which is set free. In the course thereof, the pH falls to a value of 3.5, for instance, and then increases again during the chlorination to a value of 6-7, for instance. If the pH should increase beyond this level, it is advisable to add a mineral acid, for example hydrochloric acid, at the same time as the last portion of sodium hypochlorite solution.

In the process according to the invention, 2,4-dinitrochlorobenzene can be used as the sole starting material. It is also possible, however, to employ a mixture of 2,4-dinitrochlorobenzene and a 2,4-dinitrophenyl alkyl ether for the saponification, by introducing the 2,4-dinitrochlorobenzene into the aqueous sodium hydroxide solution together with the 2,4-dinitrophenyl alkyl ether.

The fact that it is possible, in accordance with the process, to avoid intermediate isolation of the 2,4-dinitrophenol formed in the saponification is particularly valuable in view of the high toxicity of 2,4-dinitrophenol.

Finally, 2,4-dinitrophenol can be added to the 2,4-dinitrochlorobenzene or the 2,4-dinitrophenyl alkyl ether or the mixture of thes two compounds, at the start or after the completion of the saponification reaction. As a result of the last-mentioned alternative, the process according to the invention is also suitable for working up waste products containing 2,4-dinitrophenol and/or a 2,4-dinitrophenyl alkyl ether, for example 2,4-dinitromethoxyethoxybenzene, it being necessary for the 2,4-dinitrophenyl alkyl ethers or the mixture of 2,4-dinitrophenol and the 2,4-dinitrophenol alkyl ethers to be added not later than during the saponification reaction and it is also possible, in some cases, for the catalytic effect, which is already known, of aliphatic hydroxy compounds on the saponification of 2,4-dinitrochlorobenzene to take effect [J. Org. Chem. 43 (1978) 10, 1925-1929; and J. Am. Chem. Soc. 98, 5663 (1976)].

6-Chloro-2,4-dinitrophenol is a dyestuffs intermediate. The OH group of this compound can be replaced, for example, by chlorine with the formation of 1,2-dichloro-3,5-dinitrobenzene (German Offenlegungsschrift No. 2,001,570 (1970), B. 44 (1911) page 3730 and CA 63 (1965) 6898 h). The strongly activated chlorine atom in the 2-position of the compound thus obtained can be replaced by a large number of nucleophils, for example by cyanamide (European Patent Application No. 53,714), whereby the corresponding 5-aminobenzimidazolone is finally obtained (U.S. Pat. No. 4,246,196). A direct replacement of the OH group in 6-chloro-2,4-dinitrophenol by nitrogen nucleophils is also possible, however, for example replacement by an amino group by treatment with ammonia under pressure to give the corresponding 6-chloro-2,4-dinitroaniline (HOUBEN-WEYL, VI/1c 2 (1976), 1160), which constitutes a coupling component for the preparation of a number of disperse azo dyestuffs (German Offenlegungsschriften Nos. 2,155,866 and 2,256,314, Japanese Published Patent Application No. 72/33,481 and Japanese Preliminary Published Specification No. 72/26,417).

The examples below serve to illustrate the process according to the invention without limiting it thereto. Parts denote parts by weight.

EXAMPLE 1

203 parts of 2,4-dinitrochlorobenzene (setting point 49° C.) are saponified to 2,4-dinitrophenol in a mixture of 303 parts of 33% strength sodium hydroxide solution and 3,000 parts of water at 95° C. under an atmosphere of air. The resulting suspension, which has a pH value of 13, is adjusted to a pH value of 3.5 by adding 185 parts of 31% strength hydrochloric acid. After 10 parts of the sodium salt of a naphthalenesulfonic acid formaldehyde condensation product (dispersing agent), 1 part of iron(III) chloride and 1 part of iodine trichloride have been added, 600 parts of 13 percent strength by weight chlorine bleach liquor (containing 150 g of active chlorine per liter) are added dropwise at 10° C. in the course of 8 hours, the pH increasing meanwhile. In the course of the addition, the pH reaches a value of 6. After it has reached this value, the pH is caused to remain at this value (pH 6) by the simultaneous dropwise addition of 5-20 parts of 31% strength hydrochloric acid during the dropwise addition of the remainder of the chlorine bleach liquor. The pH of the suspension is then adjusted to a value of 1.0 by means of 170 parts of 31% strength hydrochloric acid, and small amounts of sodium hypochlorite still present are destroyed by means of 15 parts of 40% strength sodium bisulfite solution. The resulting product is then isolated by being filtered off at 10° C. 200 parts of pale yellow 6-chloro-2,4-dinitrophenol (melting point: 104°-107° C.) containing not more than about 5% of 2,4-dinitrophenol are obtained. No by-products can be detected by thin layer chromatography.

The yield of 6-chloro-2,4-dinitrophenol is 91% of theory.

EXAMPLE 2

A mixture of 183 parts of 2,4-dinitrochlorobenzene, 16 parts of 2,4-dinitrophenol and 3 parts of 2,4-dinitromethoxyethoxybenzene is saponified to 2,4-dinitrophenol in a mixture of 303 parts of 33% strength sodium hydroxide solution and 3,000 parts of water at 95° C. under an atmosphere of air. The resulting suspension i adjusted to a pH value of 3.5 by adding 185 parts of 31% strength hydrochloric acid. After 10 parts of the sodium salt of a naphthalenesulfonic acid formaldehyde condensation product (dispersing agent), 1 part of iron-(III) chloride and 1 part of iodine trichloride have been added, 650 parts of 13 percent strength by weight chlorine bleach liquor (containing 150 g of active chlorine per liter) are added dropwise at 10° C. in the course of 8 hours, the pH increasing meanwhile. In the course of the addition, the pH reaches a value of 4.5. After it has reached this value, the pH is caused to remain, during the chlorination, within the range 4–4.5 by the simultaneous addition of 36 parts of 31% strength hydrochloric acid during the dropwise addition of the remainder of the chlorine bleach liquor. The pH of the suspension is then adjusted to a value of 1.0 by means of 170 parts of 31% strength hydrochloric acid, and small amounts of sodium hypochlorite still present are destroyed by means of 15 parts of 40% strength sodium bisulfite solution. The resulting product is then isolated by being filtered off at about 10° C. 200 parts of pale yellow 6-chloro-2,4-dinitrophenol (melting point: 101°–109° C.), now only containing traces (0.5%) of 2,4-dinitrophenol, are obtained.

The yeild is 91% of theory.

EXAMPLE 3

If a mixture of 183 parts of 2,4-dinitrochlorobenzene, 16 parts of 2,4-dinitrophenol and 3 parts of 2,4-dinitromethoxyethoxybenzene is used instead of 203 parts of 2,4-dinitrochlorobenzene, and if the procedure followed is in other respects as described in Example 1, 205 parts of 6-chloro-2,4-dinitrophenol (melting point: 104°–107° C.), containing not more than 5% of 2,4-dinitrophenol, are obtained.

The yield is 93% of theory.

EXAMPLE 4 (COMPARISON EXAMPLE)

If 830 parts of 13 percent strength by weight chlorine bleach liquor (containing 150 g of active chlorine per liter) are used instead of 600 parts of 13 percent strength by weight chlorine bleach liquor, and if the procedure followed is in other respects as described in Example 1, only 186 parts of 6-chloro-2,4-dinitrophenol (melting point: 102°–105° C.) are obtained, which corresponds to a yield of 85% of theory.

EXAMPLE 5 (COMPARISON EXAMPLE)

If 1,308 parts of 13 percent strength by weight chlorine bleach liquor (containing 150 g of active chlorine per liter) are used instead of 600 parts of 13 percent strength by weight chlorine bleach liquor, and if the procedure followed is in other respects as described in Example 1, only 170 parts of 6-chloro-2,4-dinitrophenol (melting point: 104°–107° C.) are obtained, which corresponds to a yield of 77% of theory. The 2,4-dinitrophenol content is not more than about 5%.

EXAMPLE 6

If the procedure of Example 1 is followed, but with the difference that the saponification of the 2,4-dinitrochlorobenzene is carried out not only under an atmosphere of air (oxidizing agent), but additionally by means of 55 parts of 13 percent strength by weight chlorine bleach liquor (oxidizing agent) or by additionally blowing in $CO_2$-free air (oxidizing agent), 6-chloro-2,4-dinitrophenol is obtained in the same yield and in the same degree of purity as in Example 1.

EXAMPLE 7 (COMPARISON EXAMPLE)

203 parts of 2,4-dinitrochlorobenzene (setting point 49° C.) are saponified to 2,4-dinitrophenol in a mixture of 303 parts of 33% strength sodium hydroxide solution and 200 parts of water at 95° C. under a nitrogen atmosphere. The resulting suspension is adjusted to a pH value of 3.5 by adding 185 parts of 31% strength hydrochloric acid. After 10 parts of the sodium salt of a naphthalenesulfonic acid/formaldehyde condensation product (dispersing agent), 1 part of iron(III) chloride and 1 part of iodine trichloride have been added, 650 parts of 13 percent strength by weight chlorine bleach liquor (containing 150 parts of active chlorine per liter) are added dropwise at 10° C. in the course of 8 hours, the pH increasing meanwhile. Towards the end of the addition, the pH reaches a value of 6. After it has reached this value, the pH is kept at this value (pH 6) by the simultaneous dropwise addition of 5–20 parts of 31% strength hydrochloric acid and the remainder of the chlorine bleach liquor. The pH of the suspension is then adjusted to a value of 1.0 by adding 170 parts of 31% strength hydrochloric acid, and small amounts of sodium hypochlorite still present are destroyed by means of 15 parts of 40% strength sodium bisulfite solution. The resulting product is then isolated by being filtered off at about 10° C. This gives only 130 parts of 6-chloro-2,4-dinitrophenol with a black-brown appearance and a content of unsaponified 2,4-dinitrochlorobenzene which is clearly detectable in a thin layer chromatogram.

I claim:

1. A process for the preparation of 6-chloro-2,4-dinitrophenol in a high yield and in a high degree of purity by saponifying 2,4-dinitrochlorobenzene or 2,4-dinitrophenyl alkyl ethers of the formula

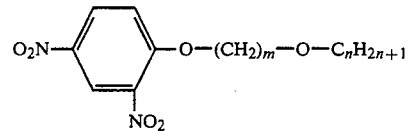

in which m denotes the number 2, 3 or 4 and n denotes the number 1 or 2, by means of aqueous sodium hydroxide or potassium hydroxide solution and chlorinating the resulting 2,4-dinitrophenol with sodium hypochlorite, which comprises chlorinating the resulting 2,4-dinitrophenol, without prior isolation as an intermediate, in aqueous suspension at a pH value of 3.5–7 by means of chlorine bleach liquor at temperatures of 5° to 20° C.

2. The process as claimed in claim 1, wherein chlorination is carried out with a 13 percent strength by weight chlorine bleach liquor (containing 150 g of active chlorine per liter) at a pH value of 4–4.5 and at temperatures of 8°–12° C.

3. The process as claimed in claim 1, wherein 2,4-dinitrochlorobenzene is subjected to said saponifying step.

4. The process as claimed in claim 1, wherein a said 2,4-dinitrophenyl alkyl ether is subjected to said saponifying step.

5. The process as claimed in claim 1, wherein the 2,4-dinitrochlorobenzene or 2,4-dinitrophenyl alkyl ether is subjected to said saponifying step in the presence of 2,4-dinitrophenol.

6. A process for the preparation of 6-chloro-2,4-dinitrophenol in a high yield and in a high degree of purity by saponifying 2,4-dinitrochlorobenzene together with 2,4-dinitrophenyl alkyl ethers of the formula

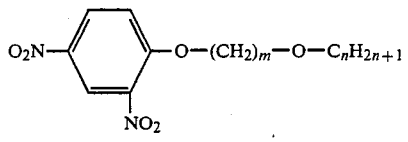

in which m denotes the number 2,3 or 4 and n denotes the number 1 or 2, by means of aqueous sodium hydroxide or potassium hydroxide solution and chlorinating the resulting 2,4-dinitrophenol with sodium hypochlorite, which comprises chlorinating the resulting 2,4-dinitrophenol, without prior isolation as an intermediate, in aqueous suspension at a pH value of 3.5–7 by means of chlorine bleach liquor at temperatures of 5° to 20° C.

7. The process as claimed in claim 6, wherein 2,4-dinitrochlorobenzene together with a said 2,4-dinitrophenyl alkyl ether is subjected to said saponifying step in the presence of 2,4-dinitrophenol.

8. The process as claimed in claim 6, wherein chlorination is carried out with a 13 percent strength by weight chlorine bleach liquor, containing 150 g of active chlorine per liter, at a pH value of 4–4.5 and at temperatures of 8°–12° C.

* * * * *